United States Patent [19]

Callahan

[11] Patent Number: 4,581,033
[45] Date of Patent: Apr. 8, 1986

[54] UNITARY INTRAOCULAR LENS PROVIDING FOUR-POINT SUPPORT

[76] Inventor: Wayne B. Callahan, 5119 Woodland Hills Dr., Brentwood, Tenn. 37207

[21] Appl. No.: 689,617

[22] Filed: Jan. 8, 1985

[51] Int. Cl.$^4$ .............................................. A61F 2/16
[52] U.S. Cl. ......................................................... 623/6
[58] Field of Search .......................................... 3/13, 1

[56] References Cited

U.S. PATENT DOCUMENTS

| | | | |
|---|---|---|---|
| 4,174,543 | 11/1979 | Kelman | 3/13 |
| 4,363,143 | 12/1982 | Callahan | 3/13 |
| 4,370,760 | 2/1983 | Kelman | 3/13 |
| 4,463,458 | 8/1984 | Seidner | 3/13 |
| 4,494,254 | 1/1985 | Lopez | 3/13 |
| 4,504,981 | 3/1985 | Walman | 3/13 |

FOREIGN PATENT DOCUMENTS 2556665  6/1977  Fed. Rep. of Germany ............. 3/13

OTHER PUBLICATIONS

"Kelman Omnifit II", advertisement Precision-Cosmet Company, Inc. 1983 (one page).

*Primary Examiner*—Ronald L. Frinks
*Attorney, Agent, or Firm*—Lowe, Price, LeBlanc, Becker & Shur

[57] ABSTRACT

An intraocular lens suitable for implantation providing four points of supporting contact within the eye and having, in unitary construction, a generally circular central lens body having, in the circular plane of the lens, centered about the 12:00 o'clock position a flat tab for manipulating the device during implantation or removal, and, in definition relative to a projection in the same plane defined by the tab and lens body, two flexible haptic lines symmetrically centered about the 6:00 o'clock position emerging between the 4:00-5:30 and 6:30-8:00 regions, respectively, which haptic lines radiate away from the central lens body following arcs defined by a common radius 0.40-0.60 times the planar radius of the central lens body; wherein said haptics symmetrically trace smooth, diverging curves ("knees") ranging from 30°-50° and proceed, respectively, parallel to lines tangent to the central lens body at points in the region 7:30-8:30 and 3:30-4:30, respectively; wherein each haptic terminates in identical, generally circular, discs ("footplates") in the common plane defined by the haptics, radiating outward and tangent to the medial surface of the haptic with said footplate having a radius ranging from 0.15-0.25 times the radius of the central lens body; wherein the outer perimeter of the two footplates and the outer perimeter of the two knees defined by said diverging curves of the haptics provide the four points of supporting contact in the anterior angle (anterior chamber placement), in the ciliary sulcus (posterior chamber placement), or in the capsular sac (posterior chamber placement).

9 Claims, 1 Drawing Figure

UNITARY INTRAOCULAR LENS PROVIDING FOUR-POINT SUPPORT

BACKGROUND OF THE INVENTION

This invention relates to intraocular lenses suitable for use as artificial lens implants.

There are many known structural arrangements for intraocular lenses. Some of these are disclosed in the following U.S. Patents. To the extent that these Patents disclose techniques of manufacture, materials and use, they are incorporated herein by reference:

U.S. Pat. No. 4,363,143—Callahan (1982);
U.S. Pat. No. 4,270,230—Poler (1981);
U.S. Pat. No. 4,249,271—Poler (1981);
U.S. Pat. No. 4,244,060—Hoffer (1981);
U.S. Pat. No. 4,174,543—Kelman (1979);
U.S. Pat. No. 4,092,743—Kelman (1978);
U.S. Pat. No. 4,159,546—Shearing (1979);
U.S. Pat. No. 4,014,049—Richards, et al. (1977);
U.S. Pat. No. 4,073,014—Poler (1978);
U.S. Pat. No. 3,975,779—Richards, et al. (1976);
U.S. Pat. No. 3,913,148—Potthast (1975);
U.S. Pat. No. 3,906,551—Otter (1975);
U.S. Pat. No. 3,866,249—Flom (1975);
U.S. Pat. No. 3,673,616—Federov, et al. (1972);

Despite these many known lens designs, the "ideal" artificial lens implant has still not been found. Perhaps the large number of such designs is suggestive of the fact that the problem is still unsolved. Ideally, an artificial lens implant would be universal, i.e., one lens design would be suitable for implantation into any human eye. Accommodation for size and orientation would be made for posterior or capsular sac placements over anterior placement; and, of course, the focal length would have to be properly selected; but the basic lens design would be unchanged. Using such a universal design, a surgeon would not have to stock all common permutations of size and design in anticipation of those situations wherein all necessary information for selecting the proper lens is available only after surgically opening the eye. That is, the ideal lens design would be capable of being fitted in the anterior or posterior chambers, or in the capsular sac, at the surgeon's discretion, or by reasons revealed during surgery. Secondly, the ideal artificial lens would exhibit a high degree of positional stability within the eye. That is, it would not be displaced by everyday vibrations and shocks to the eye, or by violent trauma. Thirdly, the ideal lens would be relatively easy and safe to insert and withdraw from the eye. Fourthly, regardless of the size of the eye into which the artificial lens is inserted, the ideal lens would exert a relative constant force against the eye tissue and that force would be predictable. This concept of constant, evenly distributed force should also act to inhibit the ideal lens from vaulting anteriorly.

The lenses disclosed by the prior U.S. patents, listed above, do not meet all of these criteria.

SUMMARY OF THE INVENTION

The present invention provides an intraocular lens suitable for use as an artificial lens implant that comes closer than known intraocular lens in meeting the "ideal" design criteria. The lens of the present invention is of one-piece construction and is structured so that one size implant can be used for the normal range of human eye sizes. The basic lens design is also capable of being fitted in the anterior or posterior chamber, or in the capsular sac. For convenience, the design parameters of the lens for anterior placement are expressly disclosed, accommodations relative to size and orientation for posterior and capsular sac placements being disclosed relative to the anterior placement embodiment.

In addition to the above-recited ideal characteristics, the lenses of the present invention are characterized by a stability which substantially precludes anterior vaulting, and by a configuration which creates its own lens glide during insertion.

In a generic sense, the intraocular lenses of the present invention are characterized in physical form by providing four points of support within the eye, and having, in unitary construction, a generally circular, central lens body having, in the plane of the lens, centered about the 12:00 o'clock position a flat tab (which may carry a bore) for manipulating the device during implantation or removal, and, in definition relative to a projection in the same plane defined by the tab and lens body, two flexible haptic lines of bilaterial symmetry about the 6:00 o'clock position emerging between the 4:00-5:30 and 6:30-8:00 regions, respectively, which haptic lines radiate away from the central lens body following arcs defined by a common radius 0.40-0.60 times the planar radius of the central lens body; wherein said haptics symmetrically trace smooth, diverging curves ("knees") ranging from 30°-5° and proceed, respectively, parallel to lines tangent to the central lens body at points in the region 7:30-8:30 and 3:30-4:30, respectively; wherein each haptic terminates in identical, generally circular, discs ("footplates") in the common plane defined by the haptics, radiating outward and tangent to the medial surface of the haptic with said footplate having a radius ranging from 0.15-0.25 times the radius of the central lens body; wherein the outer perimeter of the two footplates and the outer perimeter of the two knees defined by said diverging curves of the haptics provide the four points of support.

Further in definition of the trace demonstrated by the above-described haptics in the relax state, the medial surface, as defined by the arc of known radius, is tangent to the 6:00 position of the outer perimeter of the central lens body or is displace 0-1.00 mm outward therefrom. Relative to a planar projection of the unitary lens, including haptics, the above-defined footplate terminii of the haptics fall within an arc having a center in common with the center of the central lens body, and described by a radius 2-3 times the radius of the central lens body. The outer perimeter of the above-defined knees falls within a similarly centered arc having a radius 1.8-2.7 times the central lens body radius. Preferably said relaxed knee radius is between 0.75 and 0.95 times said relaxed footplate radius. The term "relaxed" means the planar projection of the haptics in the unflexed state. The above-defined positioning tab does not extend beyond the haptic knee.

The plane defined by the posterior surface of the central lens body and lying parallel to the circular plane of the central lens body is common with the plane defined by the haptics, or it may be vaulted anteriorly therefrom 0–1.0 mm.

Thus, the lens support structure is formed by two substantially rigid members (the so-called knees) and two very flexible members, the footplates. Taking as the center of the substantially rigid knee system an imaginary point located between the two knees (6:00 o'clock), the footplates are located approximately 120° on either side of this center. The flexure provided by the total support system permits one size of lens to fit any human anterior chamber. And because of the architecture of the entire support system, the lens remains poised in substantially the same position within this same range of human parameters. That is, the tension exerted by the long flexible members upon the eye tissue does not vary substantially throughout the range of eye sizes.

The same lens can be implanted in the posterior chamber provided that the vaulting of the central lens body is substantially zero. That is, as disclosed above, the plane of the lens and the plane of the haptics are substantially common. For lenses vaulted anteriorly, it is recommended that the posterior placement orientation to be reversed over that of the anterior chamber orientation, that is, the vaulting should be posterior, away from the plane of the iris. Lenses of identical shape, but of predetermined scale reduction in size, as that disclosed above for anterior placement, can be implanted into the capsular sac.

In summary, the following chart describes the optics, and style/fixation (placement) of the lenses of the present invention:

| STYLE | FIXATION | ANTERIOR OPTICS | POSTERIOR OPTICS |
| --- | --- | --- | --- |
| Anterior Chamber | Anterior Angle | Convex | Plano |
| Anterior Chamber | Anterior Angle | Convex | Convex |
| Posterior Chamber | Ciliary Sulcus | Convex | Convex |
| Posterior Chamber | Ciliary Sulcus | Convex | Concave |
| Posterior Chamber | Ciliary Sulcus | Convex | Plano |
| Posterior Chamber | Capsular Sac | Convex | Plano |
| Posterior Chamber | Capsular Sac | Convex | Convex |
| Posterior Chamber | Capsular Sac | Convex | Concave |

DETAILED DESCRIPTION OF THE INVENTION

Figure 1:
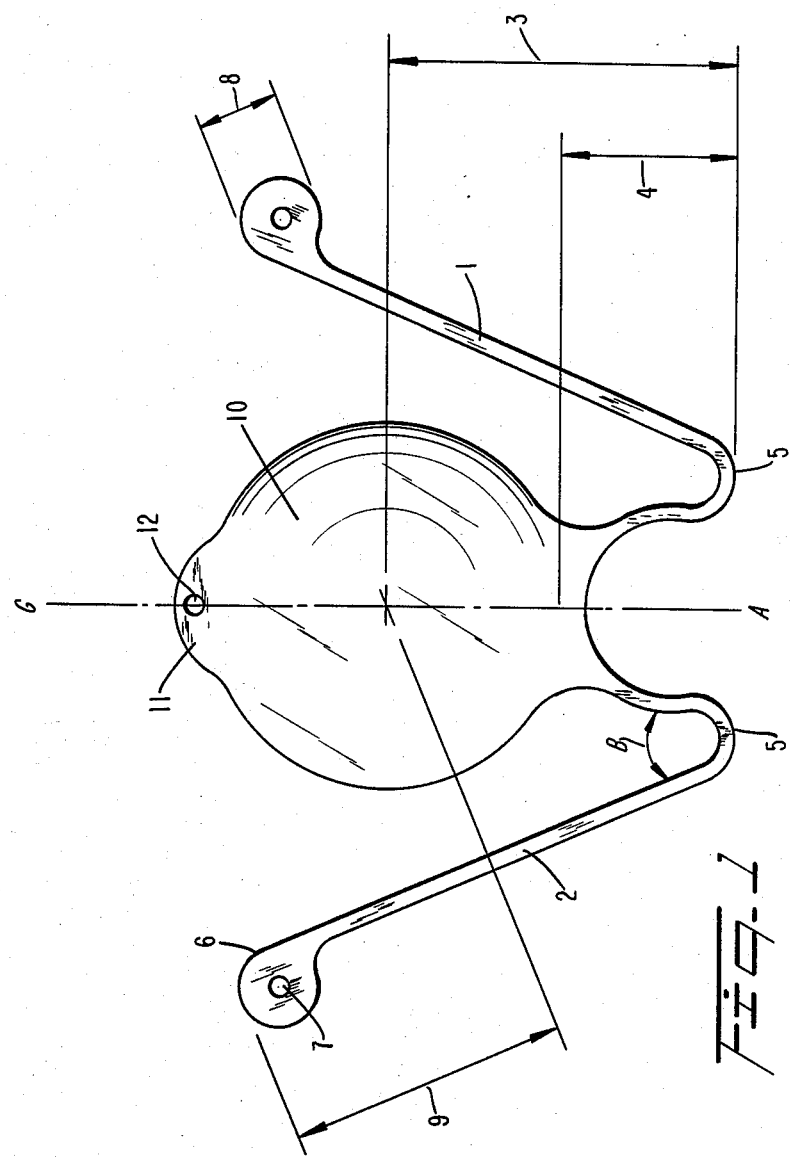
FIG. 1 represents a top view of a specific, representative embodiment of the present invention.

FIG. 1 shows a top view of a representative embodiment of the intraocular lenses of the present invention. The purpose of this drawing is to facilitate interpretation of the word description.

The lens, fabricated in an appropriate overall size, can be implanted in either the anterior chamber, posterior chamber or posterior capsule of the human eye. It is preferred that the lens be manufactured from a material capable of providing good optical characteristics while being nontoxic and stable (inert). One such material is polymethylmethacrylate. The lenses can be shaped by molding, lathe cutting, or any suitable method of manufacture. Such techniques are well known to those skilled in the art.

The lens comprises a central light focusing lens body 10. The lens body 10 can be formed to a desired, predetermined diameter and thickness. Typically, the lens body 10 would be in the range of 4.0 to 7.0 mm in diameter and 0.10 to 0.40 mm in thickness. Flat positioning tab 11 with its bore 12 is convenient during installation and withdrawal of the lens; however, there is no undue criticality as to the precise location or shape of tab 11; the only requirement being that it not inbalance the lens, or interfere with the supporting members; nor is there any criticality in the presence of tab 11; however, it is present on preferred embodiments of the present invention.

FIG. 1 demonstrates the bilateral symmetry of the lens about axis A–G. The haptic lines 1 and 2 are fabricated to a predetermined thickness and width; both dimensions typically range from 0.10–0.40 mm. The length of the first segment of the haptics 3, from the center of the central lens body 10 to the haptic's knee 5, is a function of the size of the lens body 10; typically distance 3 is in the range of 5.0 to 7.0 mm. For a lens to be implanted in the eye's anterior chamber, the nominal length 4 would be approximately 6.5 mm. The knee angles B range from 30°–50°. As disclosed above, semi-rigid knees 5 are part of the 4-point support system.

Haptic lines 1 and 2 terminate in identical footplates 6 which may carry a bore 7 which may be used to fetter under tension footplates 6 via bore 12 with an appropriate length of suture during insertions. Footplates 6 are generally circular with smooth edges and are fabricated to predetermined dimensions: diameter 0.5–2.5 mm; and thickness ranges from 0.10 to 0.4 mm. The distance 9 from the center of the central lens body 10 to the outer edge of the footplates 6 is preferably somewhat longer than the radius of the largest eye the lens would be inserted in.

As mentioned above, the lenses of the present invention can be fabricated to vault the central lens body anteriorly. The vault on a lens designed for anterior chamber implantation would typically be in the range of 0.0 to 0.70 mm; preferably 0.4 to 0.6 mm. While the thickness dimension of the haptic lines have been given above to be within the range of 0.10 to 0.40 mm, it is preferred that the haptic portion emerging from the central lens body 10 to knees 5 be somewhat thicker than the average thickness of the haptic as it runs from knees 5 to footplates 6. This is particularly true for vaulted embodiments.

Relative to bores 12 and 7, it can be seen that their size and position can be determined to achieve balance and reduce overall weight. Secondly, they provide the surgeon with a convenient point from which the lens can be manipulated during implantation or removal, for example, the lens can be grasped with a surgical implement through any of these bores, or a suture can be passed through bore 7 and stabilized via bore 12 so that the flexible footplates 6 are drawn together. In this manner the apparent width of the total lens is no greater than the central lens body 10.

The intraocular lens according to the present invention is particularly suitable for easy surgical implantation. Because the state of the art of surgical implantation of artificial lenses by qualified ophthalmic surgeons is quite high, only a basic insertion method and final positioning of this particular lens design will be discussed.

It is expected that an incision would be made along the cornea-sclera boundry. With many of the prior art regid lens having members longer than the lens body it is required that the incision be made longer than necessary to insert only the lens body. According to the structure of the present invention, the two thin flexible members 1 and 2 exhibit the characteristics of a spring. Since footplates 6 are attached to the respective flexible thin members, spring action holds the footplates into position.

For anterior chamber lens implants, the surgeon may choose to insert outer edge knees 5 first. Using this approach, the flexible members 1 and 2 are compressed towards lens body 10 and pass through an opening sized to allow insertion of lens body 10. The lens is inserted until knees 5 are resting in a groove formed by the sclera spur and the iris. As footplates 6 enter the eye and clear the incision, they will spring open until they reach the continuation of the same groove into which knees 5 were inserted. By attaching a suture through the bored portion of the flexible member footplates, and drawing the footplates together, the lens may be inserted in the opposite orientation as aforementioned.

For posterior chamber lens implantation, if knees 5 are inserted first, knees 5 will come into contact with a groove formed by the ciliary body and the iris. Once the lens is in this position, the surgeon may slip the remaining footplates behind the iris. Due to the spring action of flexible members 1 and 2 they should come to rest in the continuation of the same groove.

By attaching a suture through the bored portion of the flexible member footplates, and drawing the footplates together, the lens may be inserted in the opposite orientation as aforementioned.

To implant the lens in the posterior chamber capsular sac, the lens can be inserted from either direction and placed into the capsular sac similar to the previously outlined procedure for the posterior chamber lens implantation.

While the invention has been described in connection with what is presently considered to be the most practical and preferred embodiments, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures.

What is claimed is:

1. An intraocular lens providing four point support comprising a generally circular central lens body and two flexible members symmetrically centered bout the 6:00 o'clock position of the central lens body; wherein said flexible members emerge from the periphery of the central lens body between the 4:00–5:30 o'clock and 6:30–8:00 o'clock regions, respectively; and wherein said flexible members radiate away from the central lens body following arcs defined by a common radius 0.40 to 0.60 times the planar radius of the central lens body; and wherein said flexible members then trace smooth, diverging curves (knees) ranging from 30° to 50° and proceed, respectively, parallel to lines tangent to the central lens body at points in the regions 7:30 to 8:30 o'clock and 3:30 to 4:30 o'clock, respectively; and wherein each flexible member terminates in generally circular discs (footplates), which are oriented in the plane defined by the projection of the flexible members and the central lens body.

2. An intraocular lens accordingly to claim 1 wherein the footplates have a radius 0.15 to 0.25 times the radius of the central lens body.

3. An intraocular lens according to claim 1 wherein the outer periphery of the footplates fall within an arc having a center in common with the center of the central lens body having a radius 2.0 to 3.0 times the radius of the central lens body; and wherein the outer perimeter of the knees falls within a similarly centered arc having a radius 1.8 to 2.7 times the central lens body radius.

4. An intraocular lens according to claim 3 wherein the knee radius is between 0.75 and 0.95 times the radius of the footplate radius.

5. An intraocular lens according to claim 1 wherein the diameter of the central lens body is in the range of 4.0 to 7.0 mm.

6. An intraocular lens according to claim 1 wherein the thickness of the lens body is in the range of 0.10 to 0.40 mm.

7. An intraocular lens according to claim 1 wherein the distance from the center of the central lens body to the outside perimeter of either knee is in the range of 5.0 to 7.0 mm.

8. An intraocular lens according to claim 1 of unitary construction.

9. A intraocular lens providing four point support comprising a generally circular central lens body and two flexible members symmetrically centered about the 6:00 o'clock position of the central lens body; wherein said flexible members emerge from the periphery of the central lens body between the 4:00–5:30 o'clock and 6:30–8:00 o'clock regions, respectively; and wherein said flexible members radiate away from the central lens body following arcs defined by a common radius 0.40 to 0.60 times the planar radius of the central lens body; and wherein said flexible members then trace smooth, diverging curves (knees) ranging from 30° to 50° and proceed, respectively, parallel to lines tangent to the central lens body at points in the regions 7:30 to 8:30 o'clock and 3:30 to 4:30 o'clock, respectively; and wherein each flexible member terminates in generally circular discs (footplates), which are oriented in the plane defined by the projection of the flexible members and the central lens body; and wherein, centered about the 12:00 o'clock position, a positioning tab extending 0.5 to 2.5 mm from the central lens body.

* * * * *